(12) United States Patent
Maguire

(10) Patent No.: US 7,121,278 B2
(45) Date of Patent: Oct. 17, 2006

(54) METHOD AND APPARATUS FOR MANUAL DELIVERY OF VOLUME AND PRESSURE-CONTROL ARTIFICIAL VENTILATION

(76) Inventor: Michael David Maguire, 513 Adams St. #408, Toledo, OH (US) 43604

( * ) Notice: Subject to any disclaimer, the term of this patent is extended or adjusted under 35 U.S.C. 154(b) by 865 days.

(21) Appl. No.: 10/055,562

(22) Filed: Jan. 23, 2002

(65) Prior Publication Data

US 2002/0139369 A1 Oct. 3, 2002

Related U.S. Application Data

(60) Provisional application No. 60/263,426, filed on Jan. 23, 2001.

(51) Int. Cl.
*A62B 16/08* (2006.01)

(52) U.S. Cl. .................. 128/205.14; 128/204.28; 128/205.13; 128/205.16; 128/205.17

(58) Field of Classification Search ............ 128/205.28, 128/204.28, 205.14, 205.15, 205.16, 205.17; 604/37, 142, 212, 213, 214, 215, 216, 217; 417/234, 305, 472

See application file for complete search history.

(56) References Cited

U.S. PATENT DOCUMENTS

| | | |
|---|---|---|
| 4,037,595 A | 7/1977 | Elam |
| 4,077,404 A | 3/1978 | Elam |
| 4,121,580 A | 10/1978 | Fabish |
| 4,239,038 A | 12/1980 | Holmes |
| 4,374,521 A | 2/1983 | Nelson et al. |
| 4,501,271 A | 2/1985 | Clifton et al. |
| 4,774,941 A | 10/1988 | Cook |
| 4,782,831 A | 11/1988 | Gallant |
| 4,821,713 A | 4/1989 | Bauman |
| 4,870,962 A | 10/1989 | Sitnik |
| 4,898,166 A | 2/1990 | Rose et al. |
| 4,934,360 A | 6/1990 | Heilbron et al. |
| 5,067,487 A | 11/1991 | Bauman |
| 5,163,424 A | 11/1992 | Kohnke |
| 5,217,006 A | 6/1993 | McCulloch |
| 5,222,491 A | 6/1993 | Thomas |
| 5,305,739 A | 4/1994 | Gray |
| 5,359,998 A | 11/1994 | Lloyd |
| 5,427,091 A | 6/1995 | Phillips |
| 5,520,173 A | 5/1996 | Kuhn |
| 5,540,221 A | 7/1996 | Kaigler et al. |
| 5,546,934 A | 8/1996 | Kaigler et al. |
| 5,558,371 A | 9/1996 | Lordo |
| 5,628,305 A * | 5/1997 | Melker .................. 128/202.29 |
| 5,647,354 A | 7/1997 | Lakhani et al. |
| 5,711,295 A | 1/1998 | Harris, II |

\* cited by examiner

*Primary Examiner*—Weilun Lo
*Assistant Examiner*—Michael Mendoza

(57) ABSTRACT

A combination of a bellows structure (12), volume restrictor, and pressure restrictor for use on a hand-operated resuscitator is provided to enable delivery of ventilation within specific volume and pressure limitations specified by the operator. The bellows structure (12) consistently provides predictable and uniform generation of gas flow for ventilation without regard to one or two-handed technique, hand placement, or hand size. The volume restrictor, primarily comprising of an inflow obturator (20), outflow obturator (22), and placement cam (34), enables the physician to specify a specific tidal volume to be delivered, which constitutes a volume-controlled cycling capability of the invention. The pressure restrictor, primarily comprising of an outer housing (40), stopper housings (41), and a stopper (50), enables the physician to specify a specific maximum airway pressure to be exposed to the patient, which constitutes a pressure-controlled cycling capability of the invention. Combined use of the volume and pressure restricting mechanisms can provide for various additional abilities, including limiting airway pressure during volume-controlled ventilation or providing a means to detect decreasing pulmonary compliance.

11 Claims, 11 Drawing Sheets

METHOD AND APPARATUS FOR MANUAL DELIVERY OF VOLUME AND PRESSURE-CONTROL ARTIFICIAL VENTILATION

CROSS-REFERENCE TO RELATED APPLICATIONS

This application claims priority under 35 U.S.C. §119(e) from U.S. provisional application No. 60/263,426 filed Jan. 23, 2001 by Michael D. Maguire, titled Method and Apparatus for Manual Positive Pressure Delivery of Metered Artificial Ventilation.

BACKGROUND OF THE INVENTION

The following invention pertains to the art of manually providing positive-pressure artificial ventilation to the non-breathing patient, and particularly to patients suffering acute respiratory and/or cardiopulmonary arrest.

The critical role of the lungs in maintaining life is well known—most individuals are aware of the body's need for oxygen to maintain cellular metabolism and recognize the critical role of the lungs in providing the necessary amounts of oxygen to support life. When breathing stops, as it does during cardiac arrest, a vicious circle of events take place as the cells of the body attempt to survive without oxygen necessary for metabolism. These events constitute the initial phase of biological death, which rapidly progresses without prompt emergency treatment.

Accordingly, one of the first priorities in resuscitation is to establish a means to provide artificial ventilation to a patient. This begins with what is known in the art as establishing an airway, which is the process of providing an open passage for air to travel through the patient's mouth, throat, and trachea (or windpipe) to the lungs. This can initially be achieved by properly positioning the patient's head and neck.

Once an airway is established, one next provides artificial ventilation by forcing air into the patient's mouth, through the trachea, and into the lungs. When utilizing the mouth-to-mouth method of ventilation, no ventilatory device is used. This is the form of artificial breathing taught by the American Heart Association and the European Resuscitation Council as part of Basic Life Support (BLS) courses on cardiopulmonary resuscitation (CPR). However, healthcare professionals, both in-hospital (physicians, respiratory therapists, nurses, etc.) and pre-hospital (emergency medical technicians, paramedics) most often use various medical devices to provide artificial ventilation. These can include pocket masks (through which the rescuer manually blows to inflate the patient's lungs), demand valves (a mechanical device which inflates the patient's lungs with compressed oxygen when a button is manually pressed on the face mask), and automatic transport ventilators (fully automatic mechanical ventilators which deliver sequential breaths to the patient), however the device which is most frequently employed is the manual resuscitator.

Also known as an "Ambu bag" or "bag-vale-mask" (BVM), the manual resuscitator is a balloon-type device frequently portrayed on fictional or documentary medical television programs. Essentially a hand-powered air pump, the device consists of a squeezable, randomly pliable self-inflating bag (or fluid chamber) which, when squeezed by the operator, displaces air from the bag and out a port to which a face mask can be connected. More specifically, the technique to use a manual resuscitator comprises utilizing one hand to perform the combined task of maintaining proper positioning of the head (to maintain the airway), while applying pressure on the mask to form a seal between the patient's face and the mask. At the same time, the operator uses the free hand to squeeze the fluid chamber and thus displace air into the patient's lungs under positive pressure. When the fluid chamber is released the patient passively exhales, while the fluid chamber returns to its natural, inflated state in preparation for the next breath.

The manual resuscitator was originally designed in the 1930's, and over the years has fortified its position as the first-line device employed in artificial ventilation. The balloon-type design is inherently intuitive—little training is required to learn how to operate the device, and its simplicity makes it ideal for use in frantic environments commonly associated with resuscitation efforts. Its simple design also makes it inherently reliable—another highly desirable attribute for a medical device essential for resuscitation. Finally, the cost of manual resuscitators is very low, making it possible for them to be stored in readiness in highly accessible places throughout the hospital.

With these strong attributes intrinsic to the basic design of the manual resuscitator, little has been done over the years to modify it. Improvements have included utilization of new materials in the construction of the squeezable fluid chamber to facilitate a better, more comfortable grip. Other design refinements have decreased weight and decreased manufacturing cost, further contributing to the economy of disposable versions of the device.

Particularly during the past two decades, however, a number of advancements in medicine have greatly contributed to the understanding of pulmonary physiology and the pathophysiology of cardiorespiratory arrest. These advancements inspired additional clinical studies to specifically assess the performance of manual resuscitators, which have since been proven to have grave inadequacies.

One of the first problems identified was a general inability for single rescuers to simultaneously use one hand to maintain the face mask seal, use the other hand to squeeze the chamber, and generate a breath of sufficient volume (called the tidal volume). One reason for these low volumes is it is difficult to maintain an airtight seal between the face mask and the patient's face with one hand, resulting in frequent loss of a significant portion of the tidal volume to leakage. Another problem contributing to small tidal volumes is the randomly pliable nature of the skin of the fluid chamber of the device. When squeezed, areas not in direct contact with the rescuer's hand bulge out, reducing the efficiency of the manual compressing action which constitutes operation of the device. Other studies proved these deficiencies were not related to the level of training of the rescuer—paramedics, nurses, and physicians operating the device were all found to be unable to consistently provide ventilation at recommended levels. While it may seem obvious this problem can be overcome simply by providing more frequent breaths, this strategy can actually result in further decreased ventilation to the patient.

This apparent paradox, where increasing ventilatory rate may actually lead to decreased overall ventilation of the lungs, is related to a physiologic principle known as anatomic deadspace. The actual exchange of gases in the lungs, called respiration, occurs in tiny air sacks which are surrounded by a web of blood capillaries. These sacks, called alveoli, is where the blood receives oxygen from the air inhaled in exchange for carbon dioxide waste, which is exhaled. In every individual, a significant portion of a given breath remains in the mouth, throat, trachea, and the various distal airways in the lungs, which are collectively referred to as deadspace. Residual air occupying deadspace at the end of inhalation never actually reach the alveoli and therefore do not contribute to gas exchange. Accordingly, since deadspace is an anatomic constant unaffected by the size of the breath administered, when small breaths are given deadspace negates 25–35% the of total tidal volume delivered, whereas if large breaths are given deadspace consumes only 10–20% of each tidal volume. Consequently, one ventilating rapidly but with small tidal volumes is likely to deliver less effective ventilation than one would by utilizing a larger tidal volume at a slower rate.

This paradox has significant clinical implications. Frequently during resuscitation, certain blood tests are performed which measure the amount of oxygen and carbon dioxide in the blood. When such examinations reveal decreased oxygen levels or, more importantly, elevated amounts of carbon dioxide in the blood, the individual ventilating is usually prompted to increase their efforts. The natural response would be to increase the ventilatory rate, however, higher ventilatory rates have been associated with increased operator hand fatigue and inattentiveness. Consequently, tidal volumes have been observed to decrease as ventilatory rates increase. Therefore, despite increased ventilatory rate (and operator impression they are providing improved ventilation), overall ventilatory effectiveness may actually decrease, because as tidal volume decreases anatomic deadspace represents increasing proportions of each breath, which can provide a greater negative affect on alveolar ventilation than the positive effect of a higher rate.

This concept is not universally recognized among health care providers. As a result, many continue to inappropriately regard the effectiveness of the manual resuscitator as rate-dependent rather than volume-dependent.

Pursuant to findings demonstrating inability of single rescuers to generate adequate volumes, authoritative agencies recommended implementation of a two-person technique to utilize manual resuscitators—one-person to maintain a face mask seal with two hands, while the other rescuer squeezes the fluid chamber using two hands. Clinical studies performed thereafter sought to document delivery of higher tidal volumes consistent with resuscitation standards.

While increased volumes are produced by the two-person technique, clinical studies also identified significant hazards associated with the two-person technique. To compensate for the aforementioned bulging-out phenomenon during the one-handed technique, resuscitator manufacturers make fluid chambers disproportionally large. Thus when two hands are used to provide a breath, improved surface-area contact between the hands and the fluid chamber decrease the extent of outward bulging, resulting in the generation of excessive volumes, air flow rates, and airway pressures.

Generation of excessive volumes, pressures, and flow rates has been shown to cause significant hazards to the patient. One study in particular assessed the distribution of gas between the lungs and stomach in patients ventilated with manual resuscitators. Even with the one-person technique, air flow rates and airway pressures were excessive enough to cause air to preferentially enter the stomach, and at times, flow to the stomach actually was greater than the amount received by the lungs. Inflation of the stomach with air (called gastric insufflation) markedly increases the risk of patient vomiting, potentially resulting in stomach contents entering the lungs (a grave complication). In fact, the danger and incidence of gastric distention associated with the use of prior art manual resuscitators has recently been determined to be great enough to recommend utilization of child-size versions of the prior art on adult patients, since the smaller size of the child device provides a safeguard against generation of excessive volumes, pressures, and flow rates which leads to a decreased incidence of this complication. Accordingly, some resuscitation authorities now recommended that, in lieu of a truly safe and effective ventilatory adjunct, when ventilating an adult with the prior art it is preferable to compromise ventilatory effectiveness in order to achieve greater security from complications associated with adult-versions of the device.

Other measures can be employed to palliate these deficiencies of the prior art. A more definitive form of airway control involves placement of a tube (called an endotracheal tube) directly into the patient's trachea, thus isolating the airway from the gastrointestinal tract. After intubation, the face mask can be detached and the manual resuscitator directly connected to a port on the endotracheal tube. This obviates the need for active airway maintenance, provides definitive airway protection, and allows a single rescuer to use two hands to ventilate the patient.

However, endotracheal intubation is a medical procedure requiring considerable skill and experience and is usually performed by a physician, respiratory therapist, or nurse anesthetist. When performed successfully on the first attempt intubation can be completed in less than 10 seconds; however, the procedure is often successful only after multiple attempts, spanned over several minutes. Indeed, at times intubation attempts are all unsuccessful on a particular patient, perhaps due to trauma, anatomic aberrancies, and/or inexperience of the individual attempting to perform the procedure. Until the patient is successfully intubated, the aforementioned deficiencies of the prior art continue to jeopardize patient survival.

Even after successful intubation, additional studies have shown use of prior art manual resuscitators are still associated with significant risks. As previously indicated, one-handed operation results in inadequate ventilation to the patient, while two-handed operation is associated with excessive volumes, flow rates, and pressures.

One-handed operation in the intubated patient continues to result in ventilatory volumes which decrease the ability of the lungs to provide oxygen to the blood. More importantly, this also affects the amount of carbon dioxide waste the lungs can remove from the blood, which is also an absolute requirement for the sustainment of life. Carbon dioxide is created as a by-product of metabolism, and the accumulation of excessive amounts in the blood, called hypercarbia, causes an acidic pH of the blood which has various negative affects on the body. Research has definitively shown hypercarbia has several potent effects on the heart which directly contributes to decreased patient survival from cardiac arrest. Hypercarbia has been shown to increase the tendency of the heart to degenerate into a chaotic arrhythmia called ventricular fibrillation, where the heart muscle essentially quivers and produces no pumping action. Additionally hypercarbia has been demonstrated to support sustainment of ventricular fibrillation, and cause it to recur after a normal rhythm has been successfully restored. Finally, significant decreases in the effectiveness of electrical defibrillation (the treatment for ventricular fibrillation) has proven to be directly related to the presence of hypercarbia. Even in normal, beating tissue, hypercarbia has been demonstrated to immediately decrease the pumping strength of heart muscle. The only way to control hypercarbia, and thus oppose these potent effects on the heart, is to provide effective ventilation to the patient. Accordingly, since one-handed operation has been shown to generate inadequate volumes to both intubated and unintubated patients, it would appear its employment during resuscitation may contribute to patient mortality.

However, employing a two-handed technique in the intubated patient, while preventing the harmful effects of hypoventilation and hypercarbia, are associated with the aforementioned risks due to generation of excessive tidal volumes, airway pressures, and flow rates. The potential for lung injury is more pronounced when the patient is intubated since, under these circumstances, the endotracheal tube provides a sealed, direct connection between the manual resuscitator and the patient's lungs. Accordingly, excessive or over-aggressive ventilatory techniques, encouraged in-part by the intense environment of frantic resuscitation efforts, have been documented to cause traumatic injury to the lungs, particularly in pediatric and elderly patients.

In patients who are successfully resuscitated, high inflation pressures have been shown to be a contributing factor to the development of the Acute Respiratory Distress Syndrome (ARDS), the treatment of which requires sustained mechanical ventilation and intensive-care hospitalization over several weeks or months. Treatment of ARDS is extensive, extremely costly, and frequently unsuccessful. Excessive ventilatory volumes and pressures can also cause acute life-threatening lung injury through actual disruption of lung tissue. In addition to pneumothorax (collapsed lung), there have been several reports of cases where high inflation pressures generated by manual resuscitators have caused air to directly enter the bloodstream (called an air embolism), a complication which is almost invariably fatal. Even in patients with a perfusing rhythm, high airway pressures are known to decrease blood pressure, cardiac output, and oxygen delivery significantly by causing the lungs, inflated with high pressures, to compress the heart and the large blood vessels in the chest.

Another deficiency of the prior art is related to high variability of tidal volumes generated by the device. Small changes in hand position on the fluid chamber are exaggerated by the bulging-out effect, causing disproportionate changes in tidal volumes. This attribute contributes to the inability of the prior art device to provide consistent and predictable ventilation to the patient, regardless of operator technique. This has been postulated to interfere with the ability to interpret certain blood tests which assess the effectiveness of ventilation and which are fundamental measures of ventilation effectiveness.

Another disadvantage associated with breath-to-breath inconsistency is an inability to detect certain life-threatening conditions which are associated with increasing lung resistance. The presence of a life-threatening lung injury (e.g., tension pneumothorax) may be detected early by noticing a requirement for progressively increasing ventilatory pressures to achieve delivery of a specific tidal volume. With marked breath-to-breath variation associated with the prior art, this condition is likely to be apparent only after advanced progression of the injury begins to contribute to circulatory collapse and appearance of other ominous physical findings. Late identification of such underlying injuries further jeopardizes the patient and complicates treatment.

Another challenge in resuscitation is monitoring placement of the endotracheal tube. The trachea, after it descends from the throat, bifurcates into two main branches each of which go to one of the two lungs. The first concern with the placement of the endotracheal tube is to be sure it has been positioned in the trachea instead of the esophagus (which leads to the stomach). While several techniques to detect carbon dioxide (which is not present in quantity in the stomach) provides assurance the tube has been placed in the trachea, aside from interrupting resuscitation to obtain a chest X-ray there is no way to readily assess exact placement of the endotracheal tube within the trachea. This is a significant concern; if the tube is advanced or displaced too far, the end of the tube may progress beyond the bifurcation and thus only one lung will be ventilated (probably resulting in patient death if not recognized). Due to the aforementioned breath-to-breath variability of the prior art, this condition, also marked by increased pressures associated with the delivery of a specific volume, is not likely to be obvious via the operation of the prior art.

Accordingly, one can see the prior art manual resuscitator, while simple and inexpensive in design and operation, has multiple barriers to the consistent delivery of safe and effective artificial ventilation. Its use in unintubated patients either results in inadequate ventilation and hypercarbia with the one-person technique (or if a child-size device is employed), or the unacceptable risk of gastric insufflation and aspiration of vomitus associated with the two-person technique with the full-sized adult device. When used on intubated patients employment of a one-handed technique contributes to hypoventilation and hypercarbia, the latter of which has been proven to have several potent affects on the heart which directly contribute to increased mortality from cardiac arrest. When two-handed operation is used on intubated patients, the lack of an ability to guard against the generation of excessive airway pressures and volumes has been demonstrated to result in circulatory depression and a significant incidence of lung injury, the latter of which results in further complications, increased hospitalization, and/or death. Furthermore, breath-to-breath variability associated with the prior art results in unpredictable and inconsistent ventilation (affecting the ability to interpret certain blood tests), and decreases or inhibits the sensitivity for one to detect progressively increasing pulmonary resistance to ventilation, which can be indicative of endotracheal tube displacement or the presence of underlying life-threatening intrathoracic injury.

Thus, it can be seen there is a need for a device which shares beneficial attributes of the prior art (simplicity, reliability, affordability, and disposability) while offering new capabilities which address the several performance inadequacies which have been proven through clinical studies. There is a need for a device which can guard against the hazards associated with hypoventilation and hypercarbia by consistently providing predictable volumes of air without regard for hand placement, the size of a rescuer's hands, or the number of hands employed for operation. There is a need for a device which can provide safeguards against the generation of excessive volumes and airway pressures which have been demonstrated to contribute to gastric insufflation, circulatory depression, complications, extended hospitalization, and fatal lung injury. Finally, there is a need for a device which can decrease breath-to-breath variability in volume to facilitate a predictable level of artificial ventilatory support, enable more accurate interpretation of blood test results, and contribute to early identification of decreased lung compliance secondary to life-threatening intrathoracic injury or clinically significant displacement of an endotracheal tube.

SUMMARY OF THE INVENTION

In accordance with the present invention an improved design for a manual resuscitator is provided comprising a bellows incorporated into the squeezable fluid chamber which prevents outward bulging of the bag during operation, a volume restrictor which enables the operator to pre-select a specific tidal volume to be delivered with each breath, and a pressure restrictor which enables the operator to pre-select a specific maximum airway pressure to which the patient will be exposed.

Several objects and advantages of the invention are:
(a) to provide a bellows which enables uniform and predictable compression of the fluid chamber without regard to hand placement, size of the operator's hands, or use of one or two hands for operation;
(b) to provide variable rates of air displacement depending on the volume delivered, whereby smaller volumes intended for infants and pediatric patients require a greater relative movement of the bellows (thus providing more precision) compared to larger volumes provided to adult patients;
(c) to provide a ramped flow rate when used on adult patients, whereby low flow rates are provided at the beginning of a breath and slowly increase toward end-inspiration, which improves distribution of gas in the lung;
(d) to consistently provide full, effective, and uniform tidal volumes without regard to technique, thus allowing a physician to prescribe a specific and predictable degree of ventilatory support tailored to the patient's specific physical attributes and underlying illness;
(e) to provide safeguards to prevent patient harm caused by the delivery of excessive tidal volumes, airway pressures, and flow rates;
(f) to enable assertive delivery of large tidal volumes without jeopardizing patient safety, thus providing safer, more effective ventilation;
(g) to provide consistent volumes with each breath, increasing the uniformity of airway pressures sensed by the operator and accordingly the ability to detect progressively increasing airway resistance, which also increases the clinical applicability of certain monitoring tests;
(h) to provide an ability to prescribe a specific maximum airway pressure to which the patient will be exposed;
(i) to enable adequate tidal volumes to be administered to unintubated patients at low airway pressures, thus decreasing the incidence and significance of gastric insufflation and risk to the unprotected airway;
(j) to provide a new ability to detect progressively increasing airway pressure by combining the use of both volume and pressure safeguard mechanisms; and
(k) to provide an improved ability to detect underlying intrathoracic injuries and/or a displaced endotracheal tube through detection of decreasing pulmonary compliance.

Further objects and advantages will become apparent upon consideration of the drawings and detailed description of the invention.

DESCRIPTION OF THE DRAWINGS

FIG. 1a shows the bellows in a fully inflated condition, FIG. 1b shows bellows in a partially inflated condition, and FIG. 1c illustrates the bellows in the deflated condition.

FIG. 2a shows a cone-shaped inflow obturator which contains a number of inflow fluid conduits to enable flow of fluid through the resuscitator. FIG. 2b shows a donut-shaped inflow obturator spacer with an opening or lumen in the center to permit fluid flow. FIG. 2c shows a combination cone-shaped inflow obturator together with the inflow obturator spacer, the two of which may be permanently joined into a single component. FIG. 2d shows an outflow obturator, which, other than orientation, is identical to the inflow obturator.

FIG. 3a shows a disk-shaped placement selector, which contains numerous fluid conduits to permit fluid flow. FIG. 3b shows a ring-shaped inflow selector spacer, and FIG. 3c shows these two components assembled together with the addition of a placement cam, all three of which form a single assembly.

FIG 4a demonstrates how the inflow and outflow obturators are positioned onto the placement cam. FIG. 4b shows complete assembly of the volume restrictor. FIG. 4c shows the combined assembly of the volume restrictor and the example embodiment of the bellows, with the addition of a fluid chamber skin.

FIGS. 10a–b also show an example embodiment of a controller of the pressure restrictor which employs a compressible spring which surrounds the outer housing of the pressure restrictor.

Figure 1A:
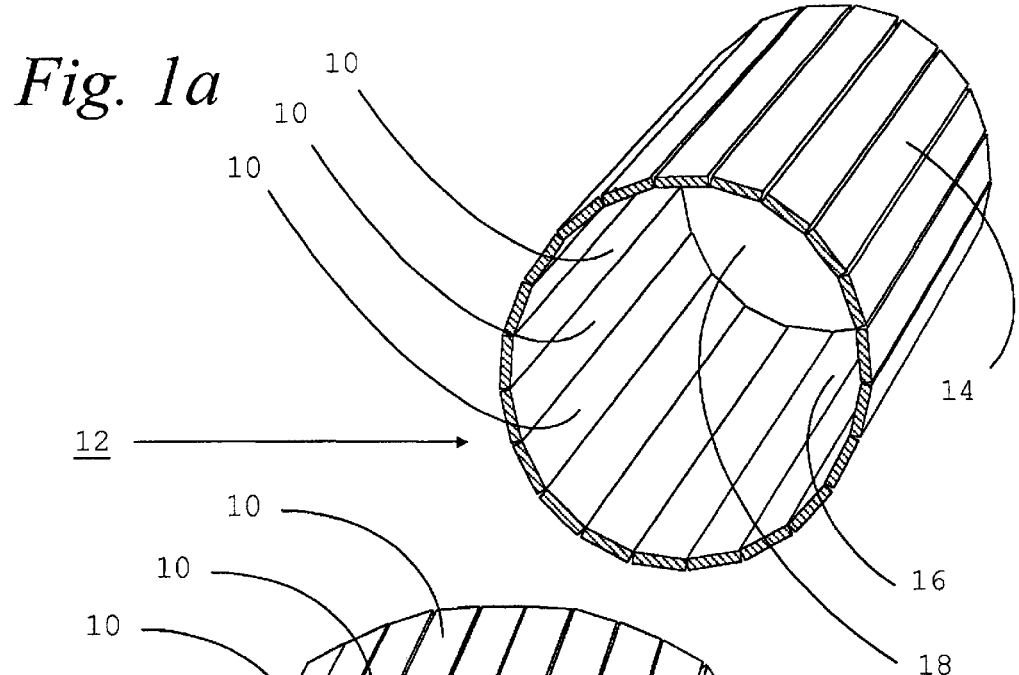
In FIGS. 1a–c of the drawing figures an example embodiment of a cylindrically-shaped bellows is shown.

| REFERENCE NUMERALS IN DRAWINGS | |
|---|---|
| Bellows Components | |
| 10 | structural member |
| 12 | bellows structure |
| 14 | bellows structure exterior surface |
| 16 | bellows structure interior surface |
| 18 | fluid chamber |
| Volume Restrictor Components | |
| 20 | inflow obturator |
| 20a | inflow obturator center bore |
| 21 | inflow obturator fluid conduit |
| 22 | outflow obturator |
| 22a | outflow obturator center bore |
| 23 | outflow obturator fluid conduit |
| 24 | inflow obturator spacer |
| 25 | inflow obturator spacer lumen |
| 30 | placement selector |
| 31 | placement selector fluid conduit |
| 32 | inflow selector spacer |
| 33 | inflow selector spacer lumen |
| 34 | placement cam |
| Pressure Restrictor Components | |
| 40 | outer housing |
| 41 | stopper housing |
| 42 | housing fluid conduits |
| 43 | stopper notch |
| 44 | controller channel |
| 45 | pressure channel |
| 50 | stopper |
| 51 | pressure header spar |
| 52 | pressure header |
| 53 | controller header spar |
| 54 | controller header |
| 60 | controller spring |
| 61 | stopper header |
| 62 | level header |
| 63 | controller level |
| 64 | open-point stop |
| 65 | closed-point stop |
| Other Components | |
| 77 | inflow one-way valve |
| 88 | outflow one-way valve |
| 99 | bellows skin |

DESCRIPTION OF THE INVENTION

Figure 1B:
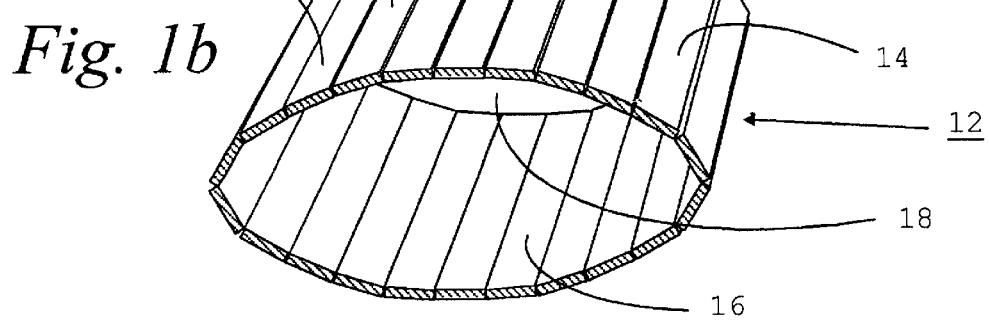
Figure 1C:
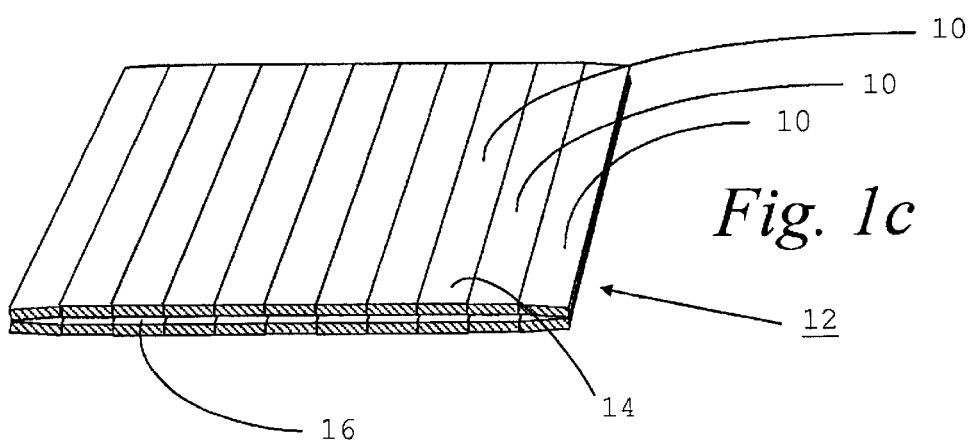

In FIG. 1 an example embodiment of a bellows is depicted. A plurity of rectangular structural members 10 can be seen to be coupled together along their long axis, whereby the combination of all the attached structural members can collectively be regarded as a bellows structure 12. The bellows structure 12 is preferably formed into a cylindrical shape by wrapping the bellows structure 12 into a circular shape along the bellows short axis. This shape enables identification of an interior surface 16 of the bellows structure and an exterior surface 14 of the bellows structure 12. The three-dimensional space contained by the bellows structure interior surface 16 can constitute a fluid chamber 18 of a particular definitive volume. In this example embodiment, the coupling of the bellows structural members 10 is provided along those edges which meet along the bellows structure interior surface 16. Accordingly, adjacent structural members 10 may flex in a direction toward the interior of the bellows structure 12, providing for a concave curvature of the bellows structure interior surface 16 and a convex curvature of the bellows structure exterior surface 14. Conversely, this coupling of adjacent structural members 10 does not provide for flexing in a direction outward from the bellows structure 12, which would require a concave curvature of the bellows structure exterior surface 14, because this would necessarily have to result from a convex curvature along the bellows structure interior surface 16, which is not possible since this would require separation of coupled edges of adjacent structural members 10. Accordingly, in FIG. 1b the bellows structure 12 can be seen to be in a partially inflated condition, whereby the fluid chamber 18 is of a diminished volume compared to the volume of that depicted in FIG. 1a. Since outward flexing of the adjacent structural members 10 is prevented by the aforementioned coupling, an application of a compressing force on the bellows structure exterior surface 14 will result in a transition of the bellows structure 12 from the fully inflated condition in FIG. 1a to the partially inflated condition depicted in FIG. 1b. Sustained application of such a force will eventually result in transition of the bellows structure to the end-point condition depicted in FIG. 1c, whereby the bellows structure 12 is flattened into an oblong shape in the fully deflated condition. In this condition the volume contained by the fluid chamber 18 approaches zero. Transition from the deflated condition depicted in FIG. 1c back to the inflated condition shown in FIG. 1a can be provided through a variety of means, including inclusion of an elastic skin lining the bellows structure interior surface 16 and/or the exterior surface 14, or through forced inflation by a fluid under pressure.

FIG. 2 depicts three components associated with an example embodiment of a volume restrictor designed to be used in conjunction with a bellows in a resuscitator. In FIG. 2a a substantially cone-shaped inflow obturator 20 can be seen, having a number of inflow obturator fluid conduits 21 which can be seen to traverse through the cone in a direction perpendicular to the base and parallel to the vertical axis of the cone. These inflow obturator fluid conduits 21 can further be seen to be collectively arranged around the center of the cone in a circular fashion, leaving the outer circumference of the cone free of voids. In the actual center of the inflow obturator 20 is a threaded inflow obturator center bore 20a, which traverses through the inflow obturator 20 in a direction parallel to the inflow obturator fluid conduits 21.

Figure 2A:
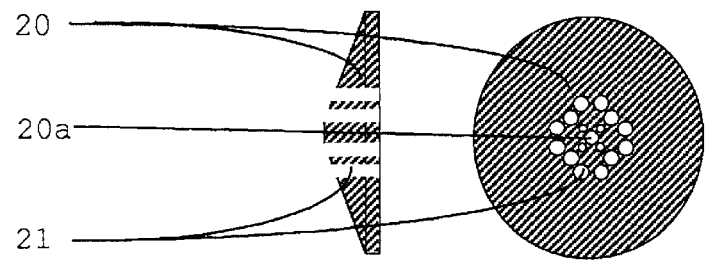
FIGS. 2a–d show components of an example embodiment of a volume restrictor.
Figure 2B:
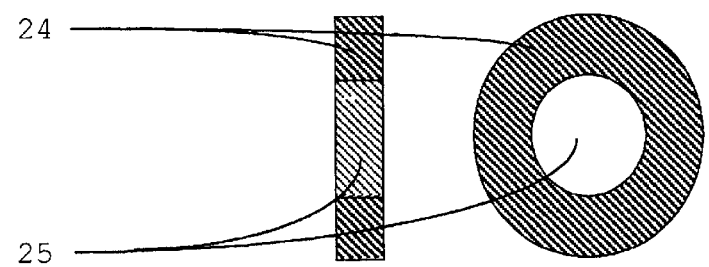
Figure 2C:
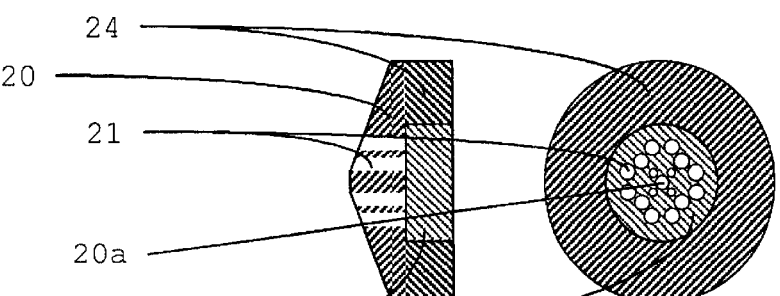

FIG. 2b depicts an inflow obturator spacer 24 which can be seen to be substantially disk or puck-shaped. An inflow obturator spacer lumen 25 is also shown in the middle of the inflow obturator spacer 24, the combination of which results in an overall ring or donut-shape of the inflow obturator spacer 24. The dimensions of the inflow obturator spacer 24 are preferably related to those of the inflow obturator 20 depicted in FIG. 2a, whereby the circumference and diameter of the inflow obturator spacer 24 is equal with that of the base of the inflow obturator 20. Additionally, the diameter of the inflow obturator spacer lumen 25 is sufficiently large enough to encircle the collective group of inflow obturator fluid conduits 21 which are arranged in a circular fashion around the center axis of the inflow obturator 20. The height of the inflow obturator spacer 24 is preferably related to the height of the inflow obturator 20, whereby the height of the inflow obturator spacer 24 is slightly greater than the height of the inflow obturator 20. FIG. 2c depicts the combination inflow obturator 20 and inflow obturator spacer 24 connected along the bases of the two components, whereby the base of the inflow obturator 20 is mated to one of the two flat-surfaced bases of the inflow obturator spacer 24. The circular circumference of the inflow obturator spacer 24 is superimposed along the same three-dimensional plane of the inflow obturator 20, thus allowing the combination of the inflow obturator fluid conduits 21 and the inflow obturator spacer lumen 25 to form a straight, continuous fluid passageway which traverses both the inflow obturator 20 and inflow obturator spacer 24.

Figure 2D:
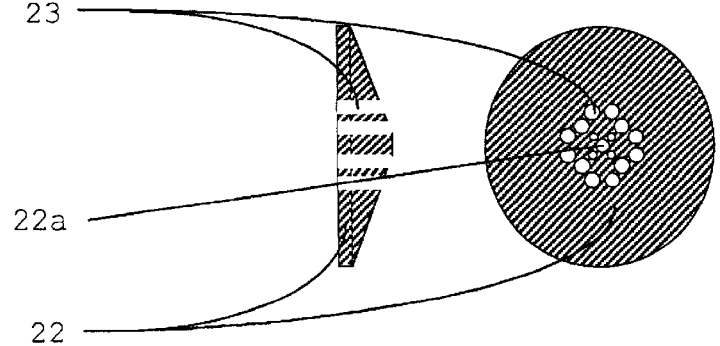

FIG. 2d depicts a cone-shaped outflow obturator 22 having outflow obturator fluid conduits 23 and an outflow obturator center bore 22a, all of which is preferably structurally identical to the inflow obturator 20, inflow obturator fluid conduits 21, and inflow obturator center bore 20a previously described. In this view the outflow obturator 22 is depicted in an orientation such that the point of the cone-shaped outflow obturator points in a direction opposite to that of the inflow obturator depicted in FIGS. 2a–c.

Figure 3A:
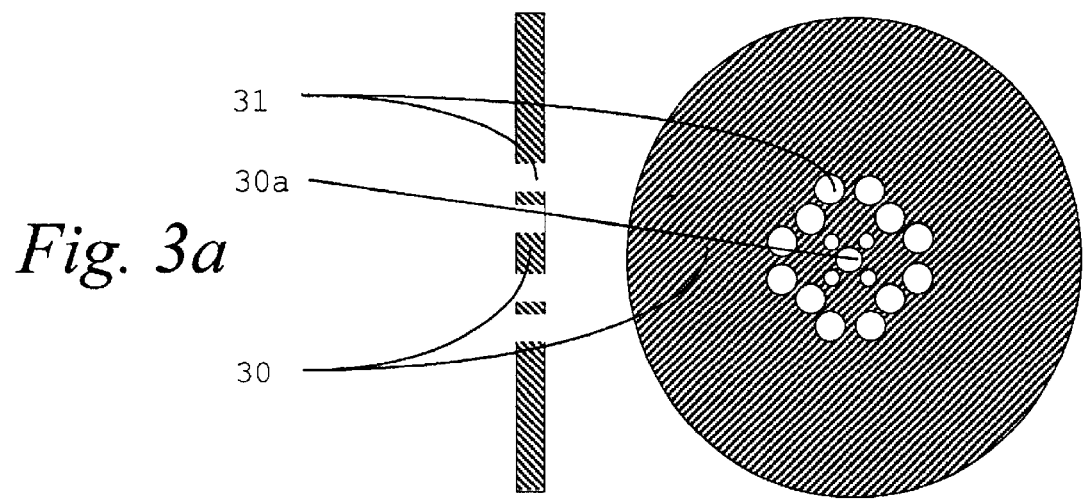
FIGS. 3a–c show additional components of another example embodiment of a volume restrictor.

FIG. 3a shows a disk-shaped placement selector 30 having a number of placement selector fluid conduits 31, which traverse through the placement selector 30 in a direction perpendicular to the flat bases of the placement selector 30. Additionally, the placement selector fluid conduits 31 are arranged in a circular fashion around the center of the placement selector 30, leaving the outer circumference of the placement selector 30 free of voids. In the actual center of the placement selector 30 is a placement selector central bore 30a which traverses through the placement selector 30 in a direction parallel to the placement selector fluid conduits 31. The overall circular diameter and circumference of the placement selector 30 is preferably identical to the diameter and circumference of both the inflow obturator 20 and inflow obturator spacer 24 depicted in FIGS. 2a–c.

Figure 3B:
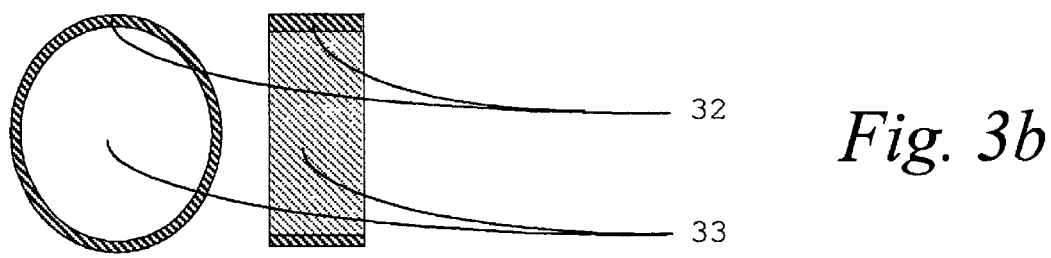

FIG. 3b shows a ring-shaped inflow selector spacer 32 having an inflow selector spacer lumen 33. The outer diameter of the inflow selector spacer 32 is preferably related to the diameter of the inflow obturator spacer lumen 25 shown in FIGS. 2b–c, whereby the outer diameter of the inflow selector spacer 32 is slightly less than the diameter of the inflow obturator spacer lumen 25, so that the inflow selector spacer 32 may freely rotate or slide to and from inward or outward within the inflow obturator spacer lumen 25. The diameter of the inflow selector spacer lumen 33 is preferably related to the placement selector fluid conduits 31 and the inflow obturator fluid conduits 21 depicted in FIGS. 2a–c, whereby the diameter of the inflow selector spacer lumen 33 is sufficiently large enough to encircle the collective arrangements of both the placement selector fluid conduits 31 and inflow obturator fluid conduits 21. The height of the inflow selector spacer 32 is preferably related to the height of the inflow obturator spacer 24 depicted in FIGS. 2b–c, whereby the height of the inflow selector spacer 32 is slightly greater than the height of the inflow obturator spacer 24.

Figure 3C:
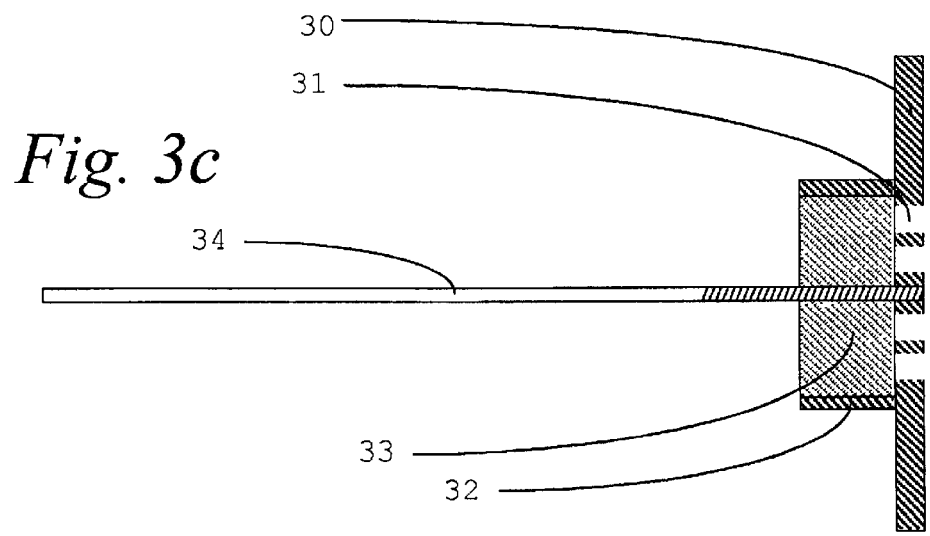

FIG. 3c depicts the combination of the placement selector 30 and inflow selector spacer 32, whereby one of the two flat bases of the inflow selector spacer 32 is attached to one of the two flat bases of the placement selector 30, wherein the respective cross-sectional center points of the two components are superimposed along the same two-dimensional plane, thus allowing the combination of the placement selector fluid conduits 31 and the inflow selector spacer lumen 33 to form a straight, continuous fluid passageway which traverses both the placement selector 30 and inflow selector spacer 33.

Also depicted in FIG. 3c is a shaft-shaped placement cam 34. The length of the placement cam 34 is preferably related to both the length of the bellows structural members 10 (shown in FIGS. 1a–c), the height of the inflow obturator 20 and outflow obturator 22 (shown in FIGS. 2a–d), the height of the inflow selector spacer 32, and the height of placement selector 30, wherein the length of the placement cam 34 is equal to the cumulative distance represented by the height of the placement selector 30, the height of the inflow selector spacer 32, the height of the inflow obturator 20, the length of the bellows structural members 10, and the height of the outflow obturator 22. The diameter of the placement cam 34 is slightly less than the diameters of the placement selector center bore 30a, the inflow obturator center bore 20a, and the outflow obturator center bore 22a. Additionally, the outer surface of the placement cam 34 is threaded to mate with the threads of the inflow obturator center bore 20a. In FIG. 3c the placement cam can be seen to fit inside the combined placement selector center bore 30a and inflow selector spacer lumen 33, wherein one end of the placement cam 34 is mounted within the placement selector center bore 30a and flush with the flat surface of the placement selector 30 which is opposite that which is in contact with the inflow selector spacer 32. In this position it can be seen the long axis of the placement cam 34 is parallel to the axis of the inflow spacer lumen 33 and placement selector fluid conduits 31.

Figure 4A:
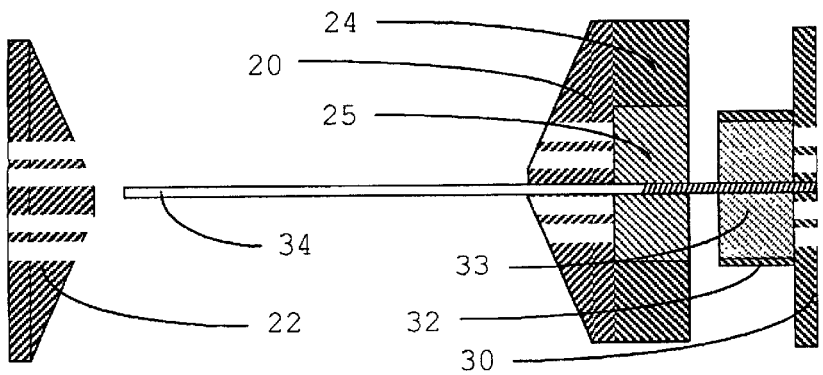
FIGS. 4a–c show sequential assembly of the invention, including all components of the example embodiment of the volume restrictor.
Figure 4B:
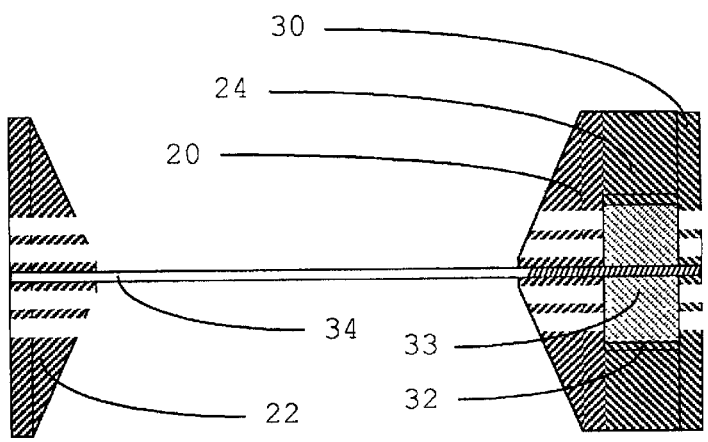
Figure 4C:
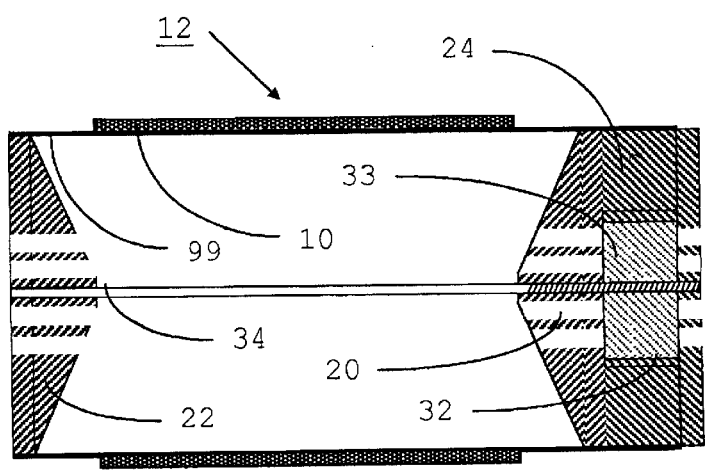

In FIG. 4a the combined assembly of placement selector 30, inflow selector spacer 32, and placement cam 34 is depicted. In addition, the outflow obturator 22 and the combined assembly of inflow obturator 20 and inflow obturator spacer 24 is also shown. The combined assembly of the inflow obturator 20 and inflow obturator spacer 24 is depicted mounted on the placement cam 34 via the inflow obturator center bore 20a (shown in FIGS. 2a–c). In FIG. 4b the same components appearing in FIG. 4a are shown. The combined assembly of the inflow obturator 20 and inflow obturator spacer 24 are shown at their final point of assembly mounted on the placement cam 34, wherein it can be seen the inflow obturator spacer lumen 33 accommodates the inflow selector spacer 32. In addition, the outflow obturator 22 is shown at its final point of assembly mounted on placement cam 34 via the outflow obturator center bore 22a (shown in FIG. 2d) at the opposite end of the placement cam 34 as the inflow obturator 20, wherein the point of the cone-shaped outflow obturator 22 points inward along the placement cam 34 toward the opposing point of the inflow obturator 20 similarly mounted on placement cam 34. FIG. 4c depicts all the components shown in FIG. 4b, with the addition of the entire bellows structure 12 comprising the collective group of structural members 10 (shown in FIGS. 1a–c) which constitute the bellows structure 12 (shown in FIGS. 1a–c). The preferably cylindrically shaped bellows is positioned over the placement cam 34 so that the center of the circular short-axis of the bellows is superimposed over the same center point of the combined assembly of the inflow obturator 20, outflow obturator 22, inflow obturator spacer 24, inflow selector spacer 32, placement selector 30, and placement cam 34. Additionally, the bellows is placed longitudinally along the long axis of the placement cam 34 so that the longitudinal position of each bellows structural member 10 (shown in FIGS. 1a–c) is directly adjacent to that part of the placement cam 34 that is between the points of the opposing inflow obturator 20 and outflow obturator 22 mounted on the placement cam 34. FIG. 4c also depicts an example use of a skin 99 which lines the bellows structure interior surface 16 (shown in FIGS. 1a–c) and which connects the bellows structure interior surface 16 with the outside circumferential edges of the outflow obturator 22 and the combined assembly of the inflow obturator 20 and inflow obturator spacer 24, wherein the combination of the skin 99, outflow obturator 22, and inflow obturator 20 constitutes a definitive, airtight fluid chamber 18.

Figure 5A:
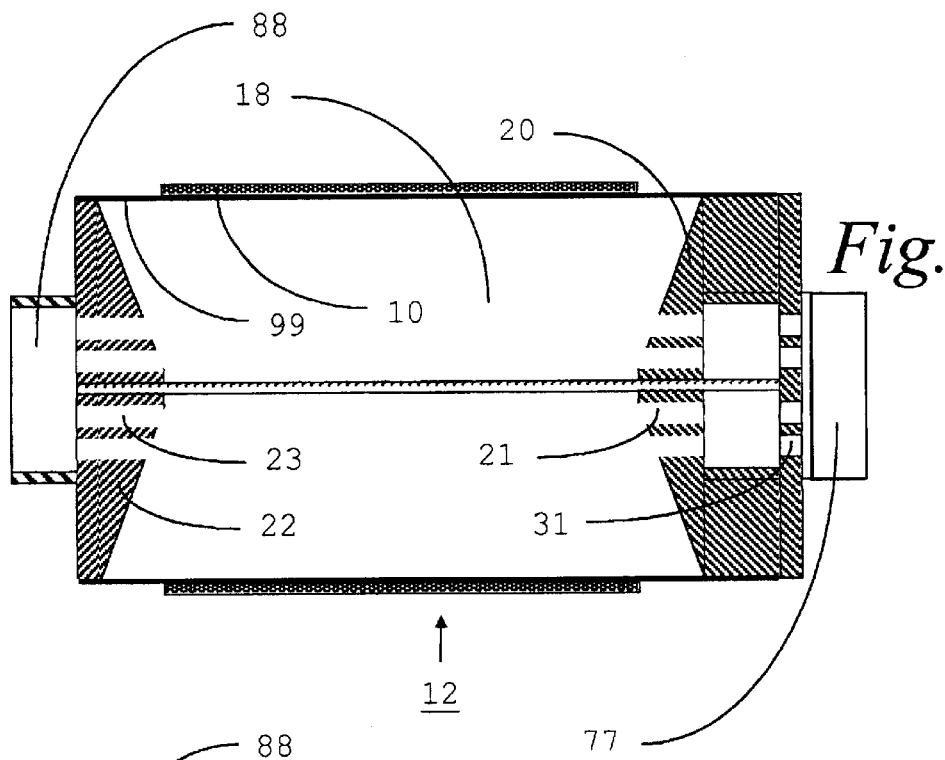
FIG. 5a shows the invention in a fully inflated condition with the volume restrictor set at the maximum allowable volume.

Now referring to FIG. 5a, the combined assembly of the invention including each of the components depicted in FIG.

4c is shown. In addition, a generic inflow one-way valve 77 is shown attached to the placement selector 30 and centered over the placement selector fluid conduits 31, thus providing an airtight cover over each of the placement selector fluid conduits 31. A similar generic outflow one-way valve 88 is shown attached to the outflow obturator 22 and centered over the outflow obturator fluid conduits 23, thus providing an airtight cover over each of the outflow obturator fluid conduits 23. The inflow one-way valve 77 will facilitate unidirectional flow through the placement selector fluid conduits 31 and inflow selector spacer lumen 33 in an antegrade direction toward the fluid chamber 18, while the outflow one-way valve 88 will facilitate unidirectional flow in the same antegrade direction outward from the fluid chamber 18 and through the outflow obturator fluid conduits 23. Thus retrograde fluid flow cannot occur into the fluid chamber 18 from the outflow fluid conduits 23, or from the fluid chamber 18 through the inflow fluid conduits 21 toward the inflow selector spacer lumen 33 and placement selector fluid conduits 31.

Figure 5B:
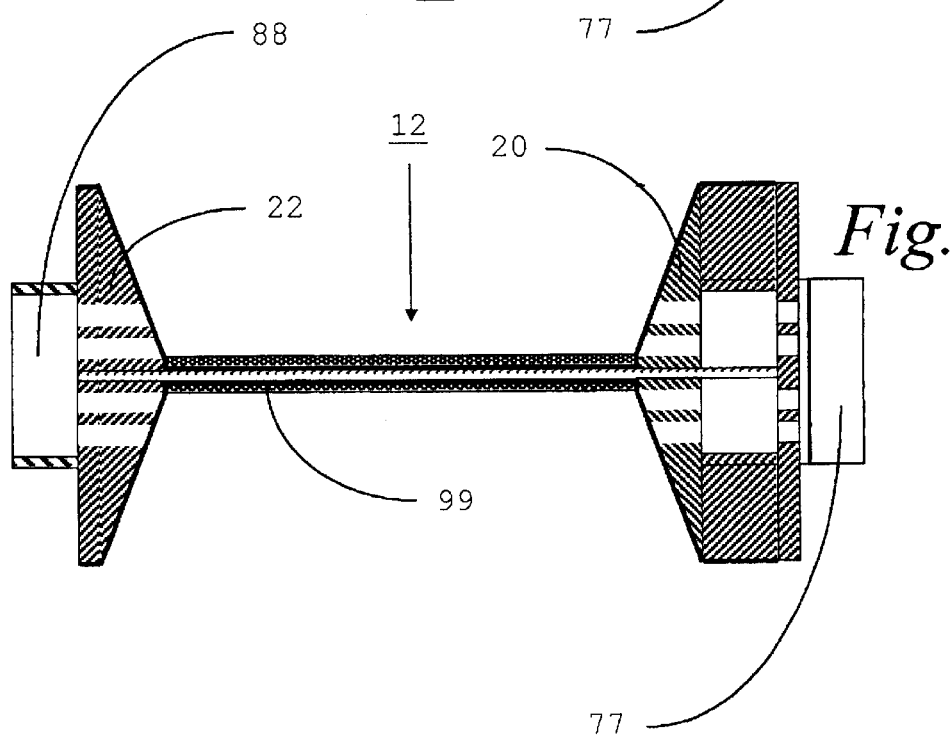
FIG. 5b shows the bellows in the fully deflated condition, whereby the obturators are positioned as to not interfere with full compression of the bellows.

Accordingly, as previously described and in accordance with FIGS. 1*a–c*, application of a compressing force onto the bellows structure 12 will transition the bellows from the inflated condition depicted in FIGS. 1*a* and 5*a* to the deflated condition depicted in FIGS. 1*c* and 5*b*, which causes a decrease in volume of the fluid chamber 18 contained by the skin 99 and bellows structure interior surface 16. Due to the aforementioned unidirectional fluid flow provided for by the inflow one-way valve 77, fluid contained in the fluid chamber 18 in the inflated condition of the invention (as shown in FIGS. 1*a* and 5*a*) will be ejected from the fluid chamber 18, through the outflow obturator fluid conduits 23 and outflow one-way valve 88 as the volume of the fluid chamber 18 is reduced to the minimum associated with the deflated condition (as shown in FIGS. 1*c* and 5*b*). Particularly note that the positioning of the inflow obturator 20 and outflow obturator 22 along placement cam 34 does not interfere or impede the range of travel of the bellows as it transitions from the inflated condition (as shown in FIGS. 1*a* and 5*a*) to the deflated condition (as shown in FIGS. 1*c* and 5*b*). In the opposite fashion, as the volume of the fluid chamber 18 re-expands into the inflated condition, fluid will flow antegrade into the fluid chamber 18 from the inflow obturator fluid conduits 21 from the direction of the inflow one-way valve 77. Accordingly, repetitive operation of the bellows results in a fluid-pumping action which provides for operation of the invention.

Figure 6A:
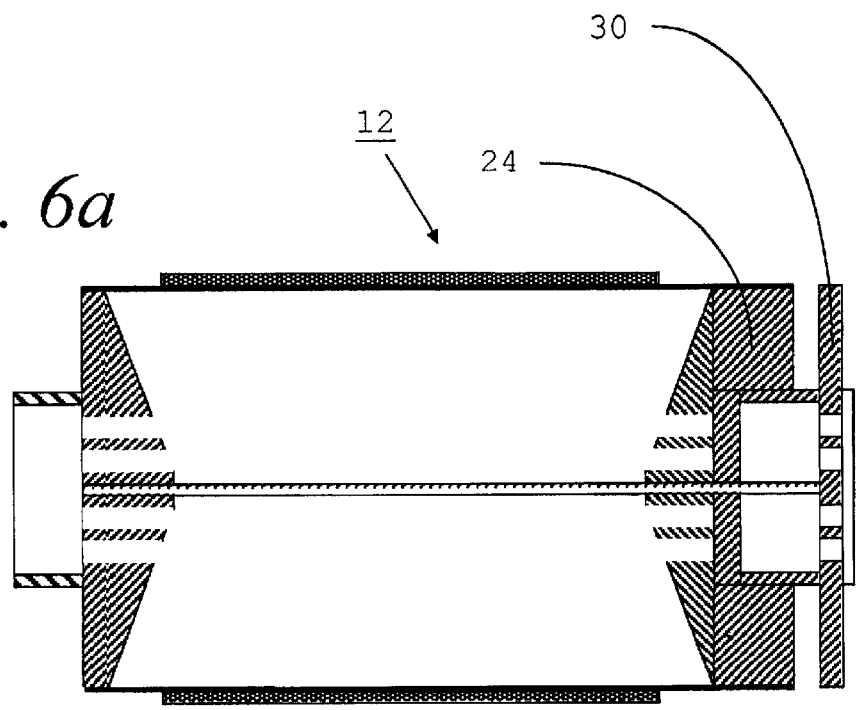
FIG. 6a provides a comparison view of the volume restrictor in the position to provide full, unimpeded volume delivery.
Figure 6B:
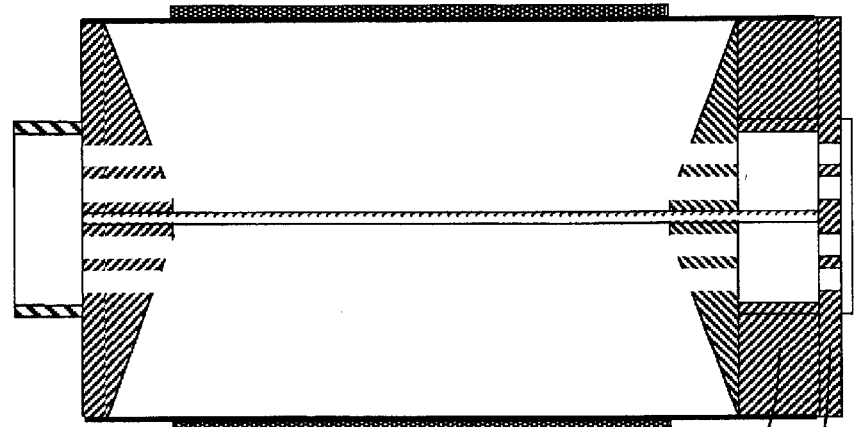
FIG. 6b shows the invention whereby the volume restrictor has been adjusted to provide delivery of a reduced volume.

In FIGS. 6*a–b* the invention appears with all the components previously outlined in FIG. 5*b*. FIG. 6*b* specifically demonstrates the result of rotating the placement selector 30 in relation to the other components of the invention. The placement selector 30 is fixed to the placement cam 34, resulting in rotation of the placement cam 34 in relation to the inflow obturator 20 and outflow obturator 22. Since the inflow obturator center bore 20*a* is threaded in a fashion which mates with the threads of the placement cam 34, rotation of the placement selector 30 causes linear movement of the combined assembly of the inflow obturator 20 and inflow obturator spacer 24 to and from along the placement cam 34. Comparing the relative location of the combined assembly of inflow obturator 20 and inflow obturator spacer 24 between FIGS. 6*a* and 6*b*, one can see the distance between the inflow obturator 20 and outflow obturator 22 within the fluid chamber 18 is shortened. Additionally, a new gap can be seen between the inflow obturator spacer 24 and the placement selector 30, which exposes a portion of the outer surface of the inflow selector spacer 32 to view.

Figure 7A:
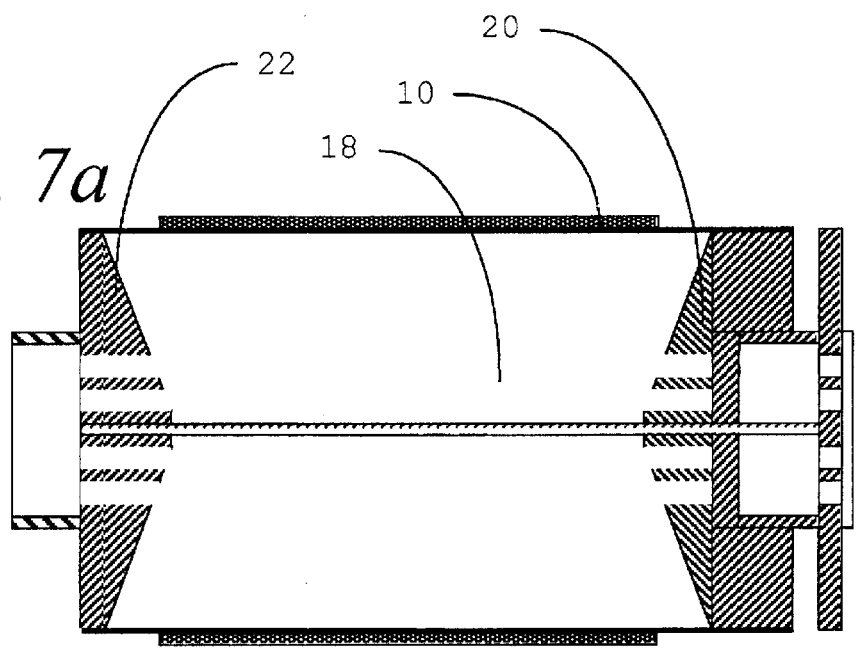
FIG. 7a shows the invention in the same condition of FIG. 6b, whereby the volume restrictor is positioned to provide for reduced volume delivery.
Figure 7B:
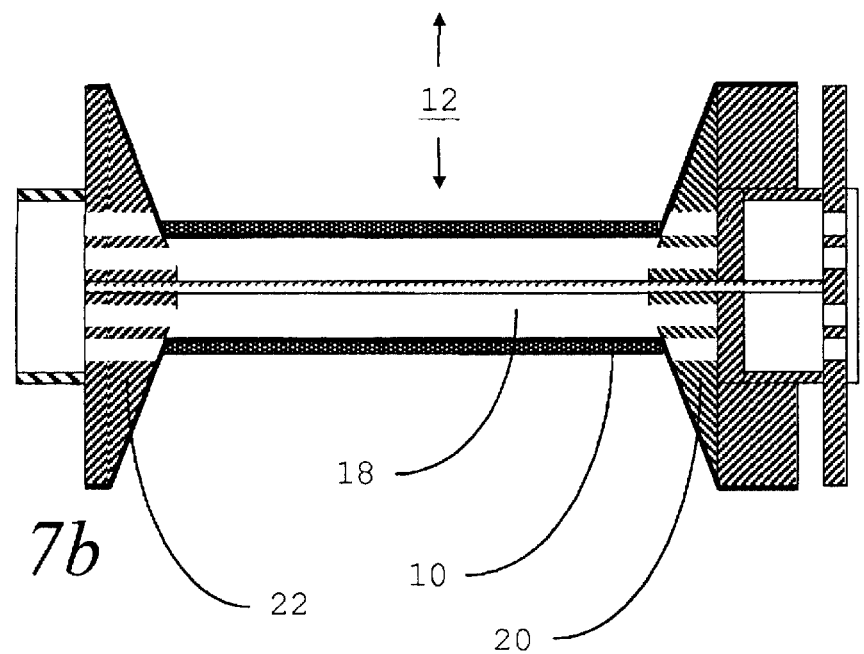
FIG. 7b shows how compression of the bellows is now partially impeded by the obturators of the volume restrictor, resulting in a residual volume inside the fluid chamber of the bellows at end-inspiration.

As previously described, application of a compressing force on the bellows results in a transition from the inflated condition toward the deflated condition. However in FIG. 7*b*, it can be seen the decreased distance between the inflow obturator 20 and outflow obturator 22 is sufficiently less than the length of the bellows structural members 10 (shown in FIGS. 1*a–c*) to interfere with travel of the bellows to the fully deflated condition. It can be further seen that as the distance between the inflow obturator 20 and outflow obturator 22 continues to be reduced by further rotation of the placement selector 30, the degree of bellows travel interference will increase further. Thus, rotation of the placement selector 30 provides a direct means to control the maximum amount of volume capable of being displaced from the fluid chamber 18 in each ventilatory cycle of the bellows.

Figure 8A:
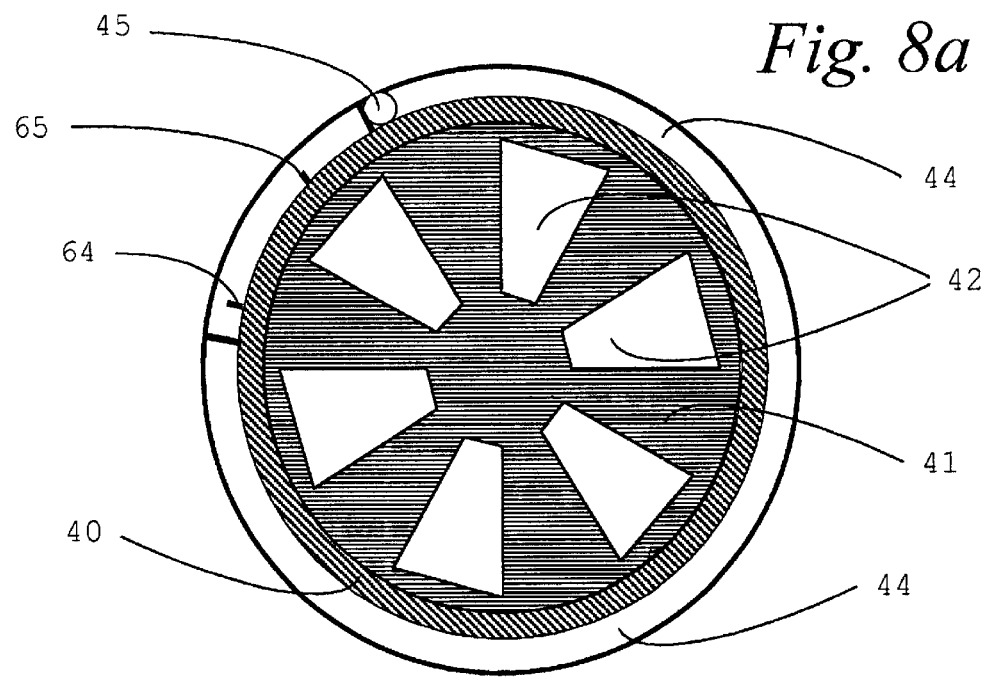
FIG. 8a shows an example embodiment of a pressure restrictor, consisting of an outer housing and internal housing fluid conduits to permit the flow of fluid through the housing.

In FIG. 8*a* components of an example embodiment of a pressure restrictor is shown, comprising a ring-shaped or short-cylindrical outer housing 40. Contained within the interior of the outer housing 40 are two disk-shaped stopper housings 41 which contain numerous housing fluid conduits 42 which permit fluid flow through the pressure restrictor. Encircling the outside surface of the outer housing 40 is a tube-shaped controller channel 44, which at one point empties into a pressure channel 45. Within the controller channel an open-point stop 64 and closed-point stop 65 can be seen as small projections which partially obstruct the lumen of the controller channel 44.

Figure 8B:
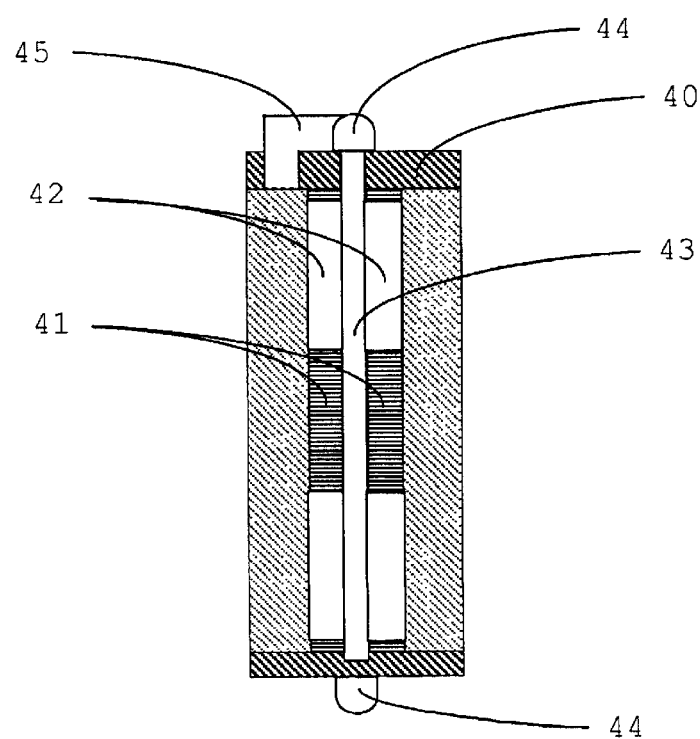
FIG. 8b shows the orientation and structure of these components from a side view.

In FIG. 8*b* a side view of the components depicted is FIG. 8*a* is provided. In this view it can be seen that a stopper notch 43 is cut away from the interior of the outer housing 40. Adjacent to each side of the stopper notch 43 is a disk-shaped stopper housing 41, containing numerous fluid conduits 42 which provide for a continuous fluid passageway from one end of the lumen of the pressure restrictor outer housing 40, though the fluid conduits 42 of one of the stopper housings 41, through the area inside the stopper notch 43, through the opposite housing fluid conduits 42, and out the opposite end of the outer housing 40 of the pressure restrictor. Also seen in FIG. 8*b* is a side view of the pressure channel 45 which communicates with the controller channel 44, wherein the side of the outer housing 40 between the stopper notch 43 and the end of the outer housing 40 which contains the pressure channel 45 (the left side, as depicted in this view) constitutes the outflow side of the pressure restrictor, while the opposite (or right side, as depicted) side of the pressure restrictor constitutes the inflow side.

Figure 9A:
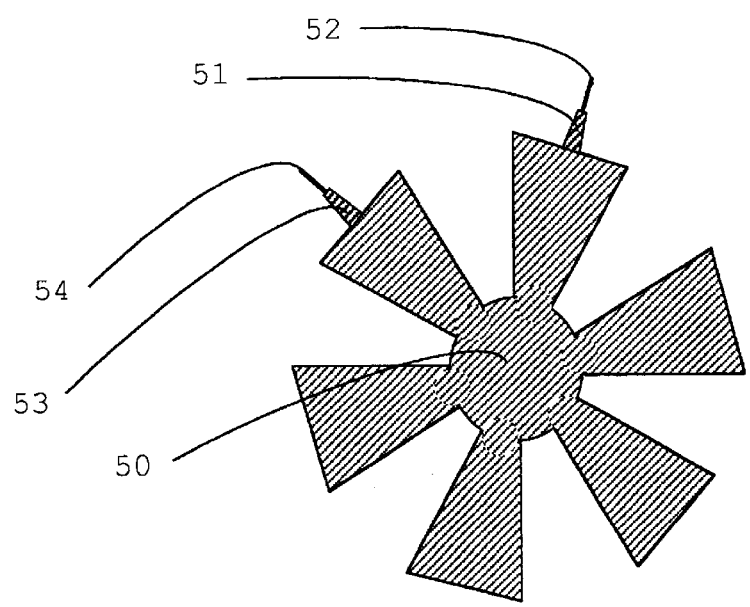
FIGS. 9a–b show a propeller-shaped stopper, which when placed adjacent to the pressure restrictor housing, provides for selective fluid flow through the housing based on the rotational position of the stopper.
Figure 9B:
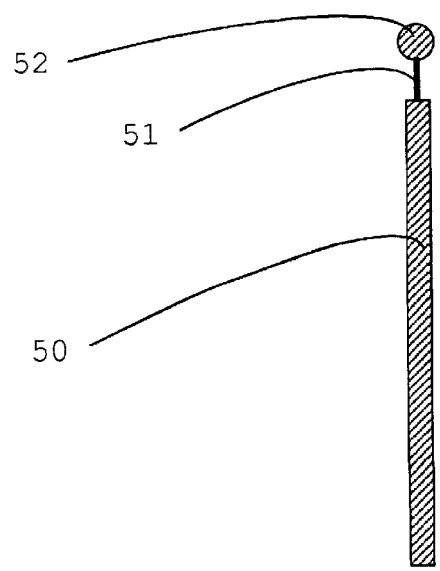

In FIG. 9*a–b* a propeller-shaped stopper 50 is depicted. The number of blades of the stopper 50 is identical to the number of stopper housing fluid conduits 42 (shown in FIGS. 8*a–b*), and are further related in shape to the shape of the housing fluid conduits 42, wherein the blades of the stopper 50 are shaped to provide variable coverage over the housing fluid conduits 42. The overall diameter of the stopper 50 is related to the diameter of the stopper notch 43 of the outer housing 40 (both shown in FIGS. 8*a–b*), wherein the diameter of the stopper 50 is slightly less than the diameter of the stopper notch 43, whereby the stopper 50 may freely rotate within the stopper notch 43. The thickness of the stopper 50 is also related to the thickness of the stopper notch 43, wherein the thickness of the stopper 50 is slightly less than the thickness of the stopper notch 43, whereby the stopper 50 is contained within the stopper notch 43 and may freely rotate within the stopper notch 43 without substantial to and from play. Attached to the outer edge of one of the stopper blades is a pressure header spar 51, which supports a pressure header 52. The shape and dimensions of the pressure header 52 is related to the internal shape and dimensions of the controller channel 44, whereby the shape and dimensions of the pressure header 52 allows movement within the controller channel 44 while also forming a substantially airtight seal between the outer edge of the pressure header 52 and the internal wall of the controller channel 44. Attached to an outer edge of one of the stopper blades adjacent to that which is attached to the pressure header spar 51 is a controller header spar 53, which supports a controller header 54. The shape and dimensions of the controller header 54 is similarly related to the internal shape and dimensions of the controller channel 44, whereby the shape and dimensions of the controller header 54 allows movement within the controller channel 44 while also forming a substantially airtight seal between the outer edge of the controller header 54 and the internal wall of the controller channel 44.

Figure 10A:
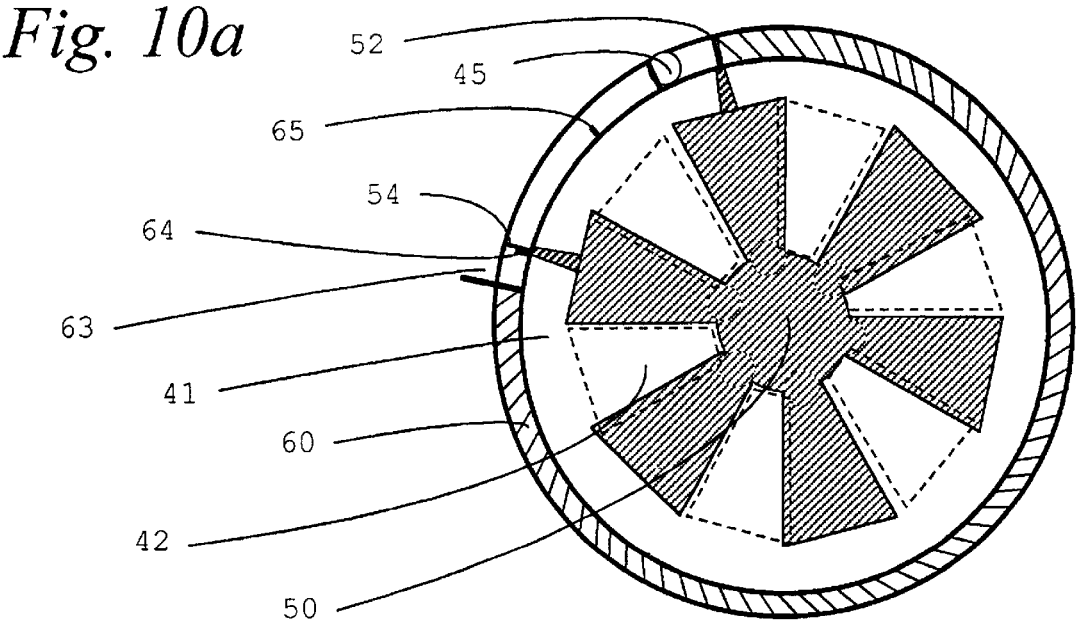
FIG. 10a shows the combined outer housing and stopper of the example embodiment of a pressure restrictor, whereby the stopper is oriented in a position to permit fluid flow through the housing via the housing fluid conduits, which are unobstructed.

In FIG. 10a, a view of the combination stopper housing 41, housing fluid conduits 42 (shown subdued), and stopper 50 is provided. It can be seen that the stopper 50, contained inside the stopper notch 43 of the outer housing 40 (shown in FIGS. 8a–b)is sandwiched between two stopper housings 41. It is also apparent in FIG. 10a the rotational orientation of the stopper 50 in relation to the housing fluid conduits 42 of the stopper housing 41 is such that the stopper 50 fails to obstruct the housing fluid conduits 42, which provides a means for fluid flow through the pressure restrictor.

Also depicted in FIG. 10a are components of an example embodiment for a controller, comprising a tube-shaped controller channel 44. Inside the controller channel 44 is a controller spring 60 which extends from its contact with a controller lever 63 through the controller channel 44 toward the opposite end of the controller channel 44, where the controller spring contacts the pressure header 52 which is also contained within the controller channel 44. The controller header 54 is also shown contained within the controller channel 44, and more specifically is in contact with the open-point stop 64. Accordingly, it can be seen the controller spring 60, which is compressed within the controller channel 44, applies a force to the pressure header 52 in a manner which rotates the stopper 50 anti-clockwise until the controller header 54 comes into contact with the open-point stop 64. In this configuration it can be seen the housing fluid conduits 42 are unobstructed, thus constituting an open condition of the pressure restrictor.

Figure 10B:
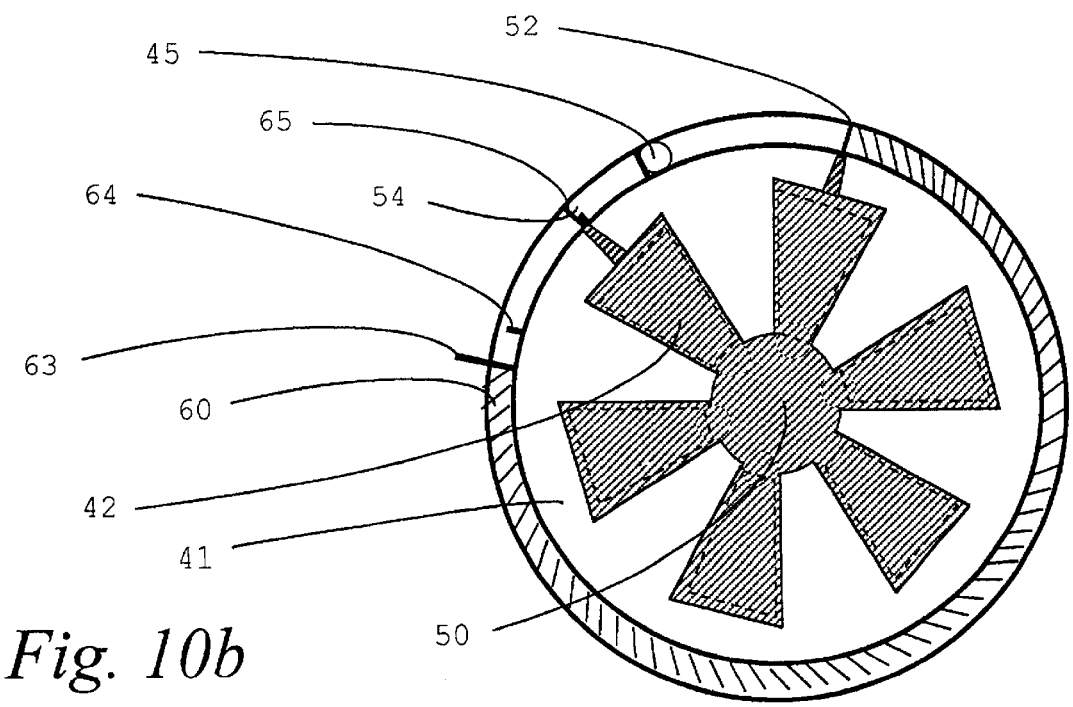
In FIG. 10b, the stopper is depicted in a rotational orientation whereby the stopper obstructs the housing fluid conduits, thus interrupting fluid flow through the pressure restrictor.

In FIG. 10b each component depicted in FIG. 10a is shown, however it can be seen the orientation of the stopper 50 is changed wherein the stopper 50 now obstructs the housing fluid conduits 42, whereby fluid flow through the pressure restrictor is interrupted. In addition, the controller header 54 is now seen to be in contact with the closed-point stop 54, while the pressure header 52 continues to be in contact with the controller spring 60. However, the overall volume of space inside the controller channel 44 between the opening to the pressure channel 45 and the pressure header 52 can be seen to be enlarged compared to the same area depicted in FIG. 10a. Accordingly, as pressure inside the outflow side of the pressure restrictor increases, this pressure is transmitted through the pressure channel 45 into the controller channel 44, where it exerts a force on the pressure header 52 which opposes the force applied to the pressure header 52 by the controller spring 60. Thus, when the pressure in the outflow side of the pressure restrictor is sufficiently great enough to overcome the compressionary resistance of the controller spring 60, the pressure header 52 will be pushed against the controller spring 60. Since the pressure header 52 is connected, via the pressure header spar 51, to the stopper 50, this movement causes the stopper 50 to rotate until the controller header 54 comes into contact with the closed-point stop 65. When the pressure inside the outflow side of the pressure restrictor drops, the controller spring 60 will return the pressure header 52, and thus the stopper 50, to the previous orientation depicted in FIG. 10a. Thus, the degree of pressure in the outflow side of the pressure restrictor directly controls opening and closing movement of the pressure restrictor.

Figure 11A:
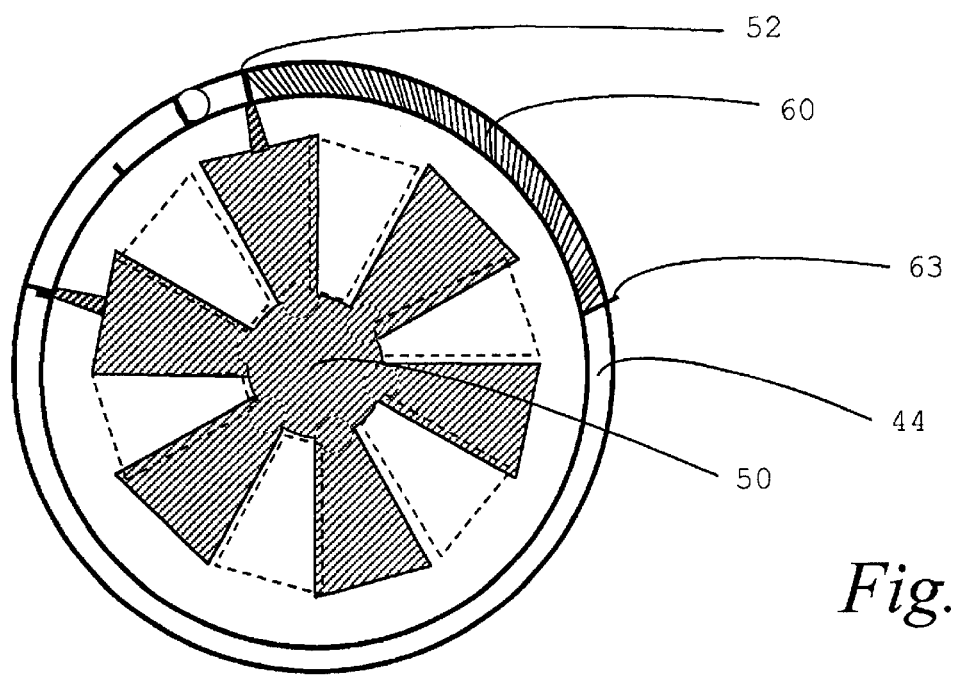
FIGS. 11a–b demonstrate the same variable positions of the stopper depicted in FIGS. 10a–b. However, in FIGS. 11a–b the pressure restrictor controller has been adjusted to a position which provides greater compression of the controller spring, changing the operational dynamics of the pressure-controller.
Figure 11B:
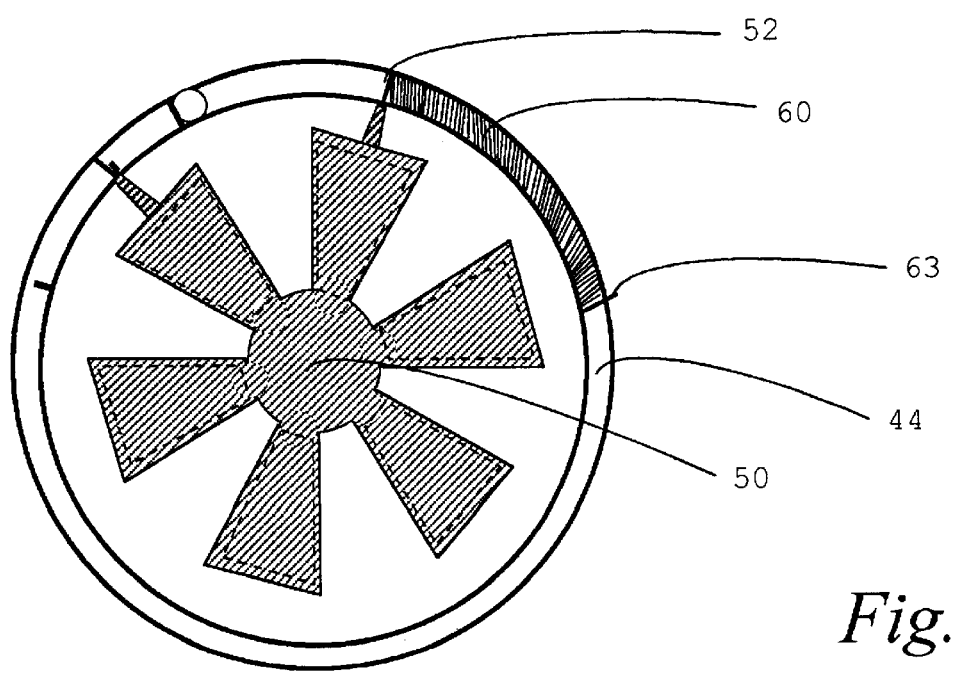

In FIG. 11a each of the components depicted in FIG. 10a are depicted, however the position of the controller lever 63 within the controller channel 44 is seen to be changed, wherein the new position of the controller lever 63 provides for considerably greater compression of the controller spring 60 contained within the controller channel 44. This causes the controller spring 60 to apply a greater force on the pressure header 52, which will thus require a greater pressure in the outflow side of the pressure restrictor to result in further compression of the controller spring 60. Accordingly, movement of the controller lever 63 provides an adjustable means to control the amount of pressure in the outflow side of the pressure restrictor required to cycle the stopper 50 between the open position and the closed position.

Thus it can be seen the example embodiment depicted provides several functional and operational advantages over the prior art. As mentioned previously, one of the disadvantages of the prior art is the amount of volume generated by the device in each breath is highly unpredictable, making it difficult for the physician prescribing its use to anticipate the degree of ventilatory support provided to the patient. In contrast, the bellows of the present invention along with the volume restrictor provides a new ability to prescribe a specific tidal volume to be delivered with each breath. As shown in FIGS. 1a–c, application of a compressionary force to the outside of the bellows will result in uniform transition from the inflated condition to the deflated condition with complete disregard to any variability in operator technique, including whether one hand or two hands are used to squeeze the bellows or the relative size of the hands of the operator. Additionally, even if hand placement on the bellows is off-center, such as toward one end of the bellows rather than in the middle, the bellows will still compress downward in a uniform movement since the coupling of the individual bellows structural members prevents the bellows from forming into any acclivital or convoluted shapes. The ability to prescribe the exact volume to be delivered to the patient in each breath will greatly contribute to safety by avoiding patient exposure to excessive volumes which can contribute to lung injury, making a single version of the invention suitable for use in patients of all age groups without the need for redundant versions of different size designed for respective use in adults, children, and infants. In addition, the definitive adjustability of the invention ensures delivery of effective ventilatory volumes to maximize oxygenation and carbon dioxide removal.

A secondary benefit of this example embodiment of the invention is its visual resemblance to the prior art. Resuscitators are most often employed during emergent life-saving efforts, and clinicians are reluctant to exacerbate the complexity of their tasks by experimenting with new, unfamiliar devices substantially different from those presently in use, and in particular any pertaining to ventilation which is to crucial to patient survival. The present invention effectively incorporates the desired functional attributes and improvements in clinical capability while substantially preserving utilization techniques predominantly in present use with the prior art, which minimizes or even eliminates the need for retraining in artificial ventilatory technique. Additionally, the invention incorporates a substantially epicyclical design having no definitive top or bottom, which facilitates rapid and immediate commencement of artificial ventilation without the need to orient the device into any specific position or configuration.

A still further advantage of the present invention is the uniform and consistent motion provided by the bellows also enhances versatility for use in patients of variable age. In particular, it can be seen in FIGS. 1a–c that the height of the cross-section of the bellows depicted in FIG. 1b is approximately one-half the height representative of the fully inflated condition depicted in FIG. 1a, that is, the condition in FIG. 1b is "half squeezed" toward the deflated condition. However, the volume of the fluid chamber depicted in FIG. 1b is substantially more than half the total volume of the fluid chamber depicted in FIG. 1a. Accordingly, a constant compressionary force applied to the bellows, resulting in a linear rate of decrease in the bellows cross-sectional dimension, will be associated with a progressively increasing rate of volume displacement as the bellows progresses toward the deflated condition. This will result in an inherently low flow rate at the beginning of a breath, with a slow and progressive increase in flow as the breath nears the end of the inspiratory cycle. This "ramped" flow pattern has been previously described to result in improved air dynamics within the lung, and was previously clinically attainable only with the use of complex, electromechanical ventilators. An additional benefit of this feature is that when smaller volumes are specified for use on infants and children (who are more susceptible to lung injury), delivery of the specified volume will require a relatively large amount of bellows movement, thus the invention provides the benefit of more precise control when being used on these patients.

The combined use of the bellows and volume restrictor also provide some unique additional clinical benefits presently unobtainable with the prior art. Since the amount of gas ventilated to the patent in each breath is constant, the operator will perceive more uniform palpable lung resistance with the delivery of each ventilation. With more experienced operators, this may facilitate earlier suspicion of life-threatening clinical conditions which are associated with progressive perceived increases in lung resistance to ventilation.

The presence of a pressure restrictor as part of the invention also provides for substantially improved clinical abilities. In infants and young children it is frequently desirable to use attainment of a specific inspiratory pressure as an endpoint to the inspiratory cycle (i.e., ventilation is pressure-controlled) in place of delivery of a specific volume with each breath (i.e., ventilation is volume-controlled). Previous versions of the prior art have included a pressure relief valve which vented excess pressure generated by the operator to the atmosphere, however operation of these "pop-off" values often interfered with delivery of effective ventilation. Alternatively, the pressure restrictor valve incorporated as part of the present invention provides the capability to restrict patient exposure to pressures greater than a specific desired maximum by blocking outward gas flow from the fluid chamber, rather than venting excess pressure to the atmosphere. This important capability also enables the pressure restrictor to be used in conjunction with the volume restrictor to allow clinicians to specify delivery of a specific volume (i.e., provide volume-controlled ventilation) to a patient while, to enhance safety, also specifying an upper limit to the airway pressure the patient is to be exposed. Accordingly, if an operator squeezes sufficiently hard on the bellows to exceed the maximum pressure, the pressure restrictor will temporarily close, instantly cutting-off gas flow to the patient. As the lungs catch up and inspiratory pressure drops back below the maximum pressure, the pressure restrictor will reopen, allowing gas flow to resume until the pressure again exceeds the maximum. Depending on the force applied by the operator, the pressure restrictor will rapidly cycle between open and closed conditions, providing a constant flow and pressure tempering or step-down function to effectively moderate airway pressure exposed to the patient. This is particularly useful for use in unintubated patients, where patient exposure to airway pressures and gas flow rates even slightly higher than those required to ventilate the lungs rapidly results in diversion of gas into the stomach (gastric insufflation)—a potentially life-threatening complication as previously mentioned. Thus the invention provides a new ability for clinicians to employ hyperventilatory techniques in intubated patients in complete safety, without the danger of causing iatrogenic lung injury associated with the prior art.

The combined use of both the volume restrictor and pressure restrictor also provides a method to objectively monitor airway resistance. During volume-controlled ventilation, the operator may progressively decrease the pressure restrictor setting until the pressure restrictor interferes with the complete delivery of the specified volume (i.e., the pressure restrictor usurps control from the volume restrictor). At this point the operator can determine from the pressure restrictor setting the approximate airway pressure required to ventilate the specified volume, after which the pressure restrictor setting can be backed-off slightly to again permit delivery of the full ventilatory volumes specified. Certain life-threatening intrathoracic injuries (e.g., collapsed lung, intrathoracic hemorrhage) are associated with progressively decreasing pulmonary compliance, which produces progressive increases in airway resistance. Use of the invention in this manner will provide rapid clinical evidence of these conditions since the increase in lung airway resistance will elevate pressures above the pressure restrictor setting. Sudden inability to deliver the specified volume will instantly alert the operator to an increase in airway resistance, which will prompt clinical reassessment of the patient's condition, enabling earlier identification and treatment of the underlying cause. This technique can be similarly be used to detect distal displacement of an endotracheal tube beyond the bifurcation of the trachea into the two mainstem bronchi which connect to each lung—airway resistance will increase if the operator attempts to deliver a specific volume, previously provided to both lungs, preferentially toward one lung.

A similar technique can also be employed during pressure-control ventilation to provide objective monitoring of pulmonary compliance. The volume selector can be tapered downward during pressure-control ventilation until the volume restrictor begins to usurp ventilatory cycling from the pressure restrictor, at which point the setting of the volume selector can be observed to approximate the volume of gas being accepted by the patient's lungs for the given pressure restrictor setting. The volume restrictor setting can then be backed-off slightly allowing pressure-control ventilation to resume. If the operator wishes to reassess lung compliance, the volume restrictor is again tapered downward to obtain another approximate determination of the volume of gas being accepted by the patient's lungs for the given pressure setting; any substantial decrease compared to the previous amount would be indicative of decreased pulmonary compliance.

Although this description describes many specific components of the invention, this should not be construed as a limitation of the scope of the invention but as merely providing an illustration of example embodiments of this invention. For example, an alternative volume restrictor could have obturators which obstruct the bellows from assuming a fully inflated condition as a means to restrict volume, rather than controlling volume delivered by preventing full deflation of the bellows. Thus the scope of the invention should be determined by the appended claims and their legal equivalents, rather than by the specific examples provided in this specification.

I claim:

1. A bellows for use in a resuscitator, comprising:
   (a) a plurality of substantially rigid adjacent structural members coupled into a bellows structure, the bellows structure havinq a long and a short axis, wherein;
      (i) the short-axis constitutes a cross-section of the bellows structure,
      (ii) the bellows structure has an exterior and an interior surface,
      (iii) the interior surface forms a fluid chamber for accommodating a fluid,
      (iv) positioning the bellows structure to provide maximum potential volume of the fluid chamber constitutes an inflated condition of the bellows,
      (v) positioning the bellows structure to provide minimum potential volume of the fluid chamber constitutes a deflated condition of the bellows, and
      (vi) a force applied to the exterior surface of the bellows structure in a direction parallel to the short axis results in a decrease in volume of the fluid chamber, resulting in a dimensional decrease of the cross-section of the bellows structure, effectively transitioning the bellows from the inflated condition to the deflated condition, such that the bellows mechanically assists movement of fluid into and out of the fluid chamber.

2. The bellows of claim 1, wherein the coupling of the structural members provides unidirectional articulation with adjacent structural members to restrict pliability of the bellows into shapes other than those inclusive or between the inflated condition and the deflated condition of the bellows structure.

3. The bellows of claim 1, wherein the bellows structure forms a substantially cylindrical shape when positioned in the inflated condition.

4. The bellows of claim 1, wherein the bellows structure forms a substantially oblong shape when positioned in the deflated condition.

5. The bellows of claim 1, further comprising a volume-restrictor for use in a resuscitator, the volume restrictor including:
   (a) one or more obturator members which obstruct transition of the bellows between the inflated condition to the deflated condition; and,
   (b) an adjustable placer to provide for selective movement of obturator members into multiple positions relative to the bellows structure, such that
      movement of the obturator members provides for variable ranges of movement of the bellows structure between the inflated condition and the deflated condition, and
      operation of the adjustable placer specifies a predetermined degree of movement of the bellows.

6. A pressure-restrictor for use in a resuscitator, comprising:
   (a) a rigid housing structure adapted to be positioned distal to a flow-generator of a resuscitator and proximal to a flow port to a patient, such that the rigid housing structure separates the flow-generator and a flow-output portion of a resuscitator,
      (i) wherein the rigid housing structure contains a number of fluid conduits to permit the flow of fluid;
   (b) a movable stopper member positioned adjacent to the housing structure, wherein the position of the movable stopper member is configured to completely, partially, or minimally obstruct the fluid conduits of the rigid housing structure; and,
   (c) an automatic controller which operates in response to pressure in the flow-output portion of a resuscitator, wherein
      (i) variability of pressure in the flow-output portion of a resuscitator causes movement of the movable stopper member in relation to the housing structure;
      (ii) movement of the movable stopper member completely, partially, or minimally obstructs the fluid conduits of the housing structure; and,
      (iii) operation of the automatic controller decreases pressure between the flow-generation and flow-output portions of a resuscitator.

7. The pressure-restrictor of claim 6, further comprising a regulator, the regulator including:
   (a) a resistance apparatus which opposes the movement of the adjustable stopper member of the automatic controller into a position which obstructs fluid flow through the rigid housing structure of the pressure-restrictor; and,
   (b) a device to vary the degree of opposition provided by the resistance apparatus, which device enables an operator to specify a predetermined pressure at which the automatic controller engages movement of the adjustable stopper member into a position which obstructs fluid flow through the rigid housing structure of the pressure-restrictor.

8. A method of providing volume-controlled manual positive-pressure artificial ventilation, comprising:
   (a) providing a manually-operated resuscitator;
   (b) providing a volume restrictor, having one or more obturator members;
   (c) selecting a predetermined configuration of the volume restrictor; and,
   (d) manually operating the resuscitator, relying on the volume restuictor and one or more obturator members to determine maximum volume delivered in each breath, to deliver substantially-equivalent volumes in each breath.

9. A method of providing pressure-controlled manual positive-pressure artificial ventilation, comprising:
   (a) providing a manually-operated resuscitator;
   (b) providing a pressure-restrictor, having an adjustable controller;
   (c) selecting a predetermined setting for the controller of the pressure-restriotor; and,
   (d) manually operating the resuscitator, relying on the pressure-restrictor to determine maximum volume delivered in each breath, to inflate the lungs to a substantially-equivalent pressure in each breath.

10. A method of monitoring pulmonary compliance and/or airway resistance during volume-controlled manual positive-pressure artificial ventilation, comprising:

(a) providing a manually-operated resuscitator;

(b) providing a volume restrictor;

(c) providing a pressure restrictor having an adjustable controller;

(d) selecting a predetermined configuration of the volume restrictor;

(e) selecting a predetermined setting for the controller of the pressure restrictor;

(f) manually operating the resuscitator, relying on the volume restrictor to determine maximum volume delivered in each breath;

(g) adjusting the controller of the pressure restrictor to a minimum point at which the pressure restrictor fails to interfere with delivery of the maximum volume specified by the volume restrictor; and, (h) making repetitive serial assessments of the ability to operate the resuscitator with delivery of the maximum volume specified by the volume restrictor without interference from the pressure restrictor, whereby development of an inability to operate the resuscitator with delivery of the maximum volume specified by the volume restrictor caused by interference from the pressure restrictor is indicative of increasing airway resistance and/or decreasing pulmonary compliance.

11. A method of monitoring pulmonary compliance and/or airway resistance during pressure-controlled manual positive-pressure artificial ventilation, comprising:

(a) providing a manually-operated resuscitator;

(b) providing a pressure-restrictor having an adjustable controller, (c) providing a volume restrictor;

(d) selecting a predetermined setting for the controller of the pressure-restrictor;

(e) manually operating the resuscitator, relying on the pressure-restrictor to determine maximum volume delivered in each breath;

(f) temporarily adjusting the volume restrictor to the earliest point at which the volume restrictor interferes with attainment of the desired maximum inflation pressure specified by the pressure-restrictor;

(g) observing the setting of the volume restrictor at which this interference occurs;

(h) restoring the volume restrictor to a setting which eliminates the observed interference; and, (i) making repetitive serial assessments of the setting of the restrictor at which interference with the pressure-restrictor occurs, particularly observing for decreased volume settings which provide for such interference, whereby a change in the setting of the volume restrictor required to induce interference with the pressure-restrictor is indicative of a change in airway resistance and/or pulmonary compliance.

* * * * *